United States Patent [19]

Graves et al.

[11] Patent Number: 5,167,811
[45] Date of Patent: Dec. 1, 1992

[54] AFFINITY CHROMATOGRAPHY USING DRIED CALCIUM ALGINATE-MAGNETITE SEPARATION MEDIA IN A MAGNETICALLY STABILIZED FLUIDIZED BED

[75] Inventors: David J Graves, Devon, Pa.; Mark A. Burns, Fairfield, N.J.

[73] Assignee: Trustees of the University of Pennsylvania, Philadelphia, Pa.

[21] Appl. No.: 845,346

[22] Filed: Mar. 4, 1992

Related U.S. Application Data

[60] Continuation of Ser. No. 668,396, Mar. 13, 1991, which is a continuation of Ser. No. 383,324, Jul. 20, 1989, which is a continuation of Ser. No. 124,308, Nov. 23, 1987, abandoned, which is a division of Ser. No. 940,833, Dec. 12, 1986, abandoned, which is a continuation of Ser. No. 906,475, Sep. 12, 1986, Pat. No. 4,675,113, which is a continuation of Ser. No. 776,739, Sep. 17, 1985, abandoned, which is a continuation of Ser. No. 675,505, Nov. 28, 1984, abandoned.

[51] Int. Cl.$^5$ .............................................. B01D 15/08
[52] U.S. Cl. .................................. 210/198.2; 210/222; 210/502.1; 210/635; 210/656; 210/695; 502/404; 502/439
[58] Field of Search ............ 210/635, 656, 695, 198.2, 210/222, 223, 502.1; 502/401, 404, 402, 439; 436/176, 182; 55/67, 100, 386

[56] References Cited

U.S. PATENT DOCUMENTS

| | | | |
|---|---|---|---|
| 2,642,514 | 6/1953 | Herkenkoff | 210/695 |
| 3,875,044 | 4/1975 | Renn | 210/635 |
| 3,922,432 | 11/1975 | Renn | 210/635 |
| 3,954,678 | 5/1976 | Marquisee | 502/403 |
| 3,985,649 | 10/1976 | Eddelman | 210/695 |
| 4,334,027 | 6/1982 | Klein | 435/182 |
| 4,352,883 | 10/1982 | Lim | 435/182 |
| 4,376,047 | 3/1983 | Pohl | 210/502.1 |
| 4,382,982 | 5/1983 | Whillans | 210/695 |
| 4,431,544 | 2/1984 | Atkinson | 210/656 |
| 4,443,339 | 4/1984 | Rosevear | 210/635 |

FOREIGN PATENT DOCUMENTS

| | | | |
|---|---|---|---|
| 53-17592 | 2/1978 | Japan | 210/695 |
| 55-51434 | 4/1980 | Japan | 210/695 |
| 55-18523 | 5/1980 | Japan | 210/695 |
| 59-222207 | 12/1984 | Japan | 210/695 |
| WO8303426 | 10/1983 | World Int. Prop. O. | 210/198.2 |

OTHER PUBLICATIONS

Snyder, Introduction to Modern Liquid Chromatography, John Wiley and Sons, Inc., 1979, New York, pp. 169-172 & 275-276.

Mikes Laboratory Handbook of Chromatographic and Allied Methods, John Wiley and Sons, New York, 1979, pages 392-420.

Margel, "Novel Effective Immunosadsorbents Based on Agarose-Polyaldehyde Microsphere Beads: Synthesis and Affinity Chromatography", Analytical Biochemistry vol. 128, No. 2, Feb. 1, 1983, pp. 342-350.

*Primary Examiner*—Ernest G. Therkorn
*Attorney, Agent, or Firm*—Woodcock Washburn Kurtz Mackiewicz & Norris

[57] ABSTRACT

Disclosed is a method of conducting affinity chromatographic separations of biomaterials which comprises contacting the biomaterial with a solid support comprising a generally spherical bead having a generally central magnetic core and a surrounding exterior coat about the core comprising a material capable of binding with the biomaterial.

7 Claims, 1 Drawing Sheet

AFFINITY CHROMATOGRAPHY USING DRIED CALCIUM ALGINATE-MAGNETITE SEPARATION MEDIA IN A MAGNETICALLY STABILIZED FLUIDIZED BED

This is a continuation of application Ser. No. 668,396, filed Mar. 13, 1991, which, in turn, is a continuation of application Ser. No. 383,324, filed Jul. 20, 1989, now abandoned., which, in turn, is a continuation of application Ser. No. 124,308, filed Nov. 23, 1987, now abandoned, which, in turn, is a division of Ser. No. 940,833, filed Dec. 12, 1986, now abandoned, which, in turn, is a continuation of Ser. No. 906,475, filed Sep. 12, 1986, now U.S. Pat. No. 4,675,113, which, in turn, is a continuation, of Ser. No. 776,739, filed Sep. 17, 1985, now abandoned, which, in turn, is a continuation of Ser. No. 675,505, filed Nov. 28, 1984, now abandoned.

BACKGROUND OF THE INVENTION

In recent years, there has been a growing awareness of separation costs as part of the total cost in chemical processes. Sherwood (Sherwood, Pigford, and Wilke, "Mass Transfer", McGraw Hill, New York, 1975), for example, has shown a linear relationship on log-log coordinates between the value of a pure substance and the reciprocal of its concentration in the crude mixture from which it was obtained. This empirical plot suggested separation costs are often the dominant portion of the total costs of the desired product. Subsequent studies emphasizing the extraordinarily low concentrations of naturally occurring biological substances and the great difficulty to purify them have shown the correlation could be extended by several orders of magnitude using data for several differing bioproducts including materials such as interferon.

The biochemical separation processes currently used for enzyme and protein purification present further difficulties. At present, they are almost without exception highly labor-intensive, slow and relatively non-selective. A typical separation would involve gel filtration, ion exchange, or selective adsorption in chromatography columns. The fragile beads used in such columns impose pressure drop limits of 1 psi or less with correspondingly low flow rates. Another common but awkward stop involves fractional precipitation of proteins followed by centrifugation and decantation. Separations based on electrical charge such as electrophoresis and isoelectric focusing offer relatively convenient ways of obtaining purified compounds at the laboratory level, but pose problems of scale up. These problems arise because the heat produced by the passage of electric current increases as the square of a dimension (i.e. as the cross section) while the surface area for heat removal goes up only linearly. Convection, band spreading, etc. also increase at high rates with increasing scale. Normally, one must stop the process and stain for proteins to see how far the separation has progressed. Attempts have been previously made to save some of the manual labor usually associated with such operations by arranging bio-separation units into a continuous processing train. Some of the units are inherently batch-oriented, however, and the elaborate tour-de-force shown by these attempts serves only to enforce the notion that new purification techniques are needed.

Among the many techniques used today in biochemical separations, perhaps the most efficient and selective is one called affinity chromatography (AC). Unlike the other separation techniques mentioned, which have typical purification factors $P_f$ (= product purity/feed purity) of 2 to 10, affinity separations in favorable cases achieve $P_f$ values of 10,000 in a single step.

Unlike all of those previously mentioned and a number of others which were not mentioned, AC does not rely on general molecular properties such as size, electrical charge or density to carry out a separation. Instead, it involves a very specific interaction between two biomolecules, one of which is chemically attached to a solid support phase and the other of which is dissolved in solution (usually aqueous). Such interactions are almost a universal feature of biomolecules. Specific examples would include binding between antibodies and antigens, hormones and receptors, enzymes and either substrates, coenzymes, inhibitors or activators, DNA and its complement (a repressor or catabolite gene activator protein for double-stranded DNA or the complement of a single strand of DNA) and messenger RNA and ribosomes.

The beauty of such biochemical pairing is that since it involves a number of simultaneous interactions between amino acid or nucleotide residues, it can be highly specific. Biomolecules typically perform their functions in the presence of thousands of different types of molecules, indicating that this specificity is both a necessary and a natural part of their character. Affinity chromatography is a broad term which involves everything from a weak interaction which simply retards one molecule's passage through a column to a strong, almost nonreversible binding to the column packing. The latter would more properly be termed a bio-specific adsorption-desorption cycle. Drastic changes in pH, ionic strength, or temperature, or the addition of a competing soluble molecule are needed in such a case to release the molecule from its complement on the solid phase. This strong binding system could be operated in a batch vessel in an adsorption-desorption mode, but in most cases a column is used whether it is needed or not. Since other molecules are not usually affected by passage through the affinity column, in theory, several columns in series could be used to recover several molecules of interest from a given fermentation broth.

Despite these enormous advantages over other bioseparation schemes, affinity chromatography still has several serious disadvantages: (1) Even when operated as a column, it is a discontinuous chromatographic or adsorption-desorption process characterized by the introduction of a "pulse" of material and the recovery of a "pulse" of product. The disadvantage of this type of operation is that the size of the sample is severely limited. Most of the time the column is in operation no product is being collected, leading to an inefficient system. (2) One cannot, in such a column, use the viscous, debris-laden suspension of broken cells from a fermentation that one might hope to. A column would almost immediately plug if subjected to such a mixture. The removal of debris and DNA (whose extremely high molecular weight has a large effect on viscosity) is still a serious problem in industrial-scale processes. (3) Since peak emergence from the column is related to time, control and automation of the process is more difficult than it is for a steady-state operation.

Recognizing these shortfalls, attempts were made to overcome these problems by devising various types of continuous chromatographic techniques. The aim was to eliminate the inefficiency of a batch operation by allowing the sample to be injected continuously and the products to be continuously withdrawn. These techniques utilized a moving chromatographic bed wherein the movement (or in some cases a simulated movement) in each case is either perpendicular to the solvent flow, allowing a number of different compounds to be purified simultaneously, or countercurrent to the flow, in which case usually only two pure components are obtained. The advantage of either variation is the relatively high throughput which can be obtained compared to repeated batch operations. The disadvantage of some of these techniques, such as the simulated moving bed, is that they require elaborate and expensive mechanical moving seals or automatic valves to operate. In addition to the added expense, the risk of contamination is high when the system is one involving biomaterials, and when it is operated over long periods of time. Also, the problem of clogging by debris is not eliminated by any of these continuous systems.

A recent development which might be used to advantage to eliminate or substantially reduce the problem of clogging while retaining the other advantages of continuous chromatography is the magnetically stabilized fluidized bed. The ordinary fluidized bed has been used in industrial processing for many years, mostly with catalytic particles which tend to foul or become. poisoned or where thermal effects are important. Above a certain critical fluid velocity, small particles of a solid become suspended in a high velocity stream and the solids suspension acts much like a fluid, permitting it to flow out of the reactor for regeneration or replacement. If the fluid velocity is increased above the critical fluidization value, undesirable effects such as bubbling and slugging occur. These cause bypassing of reactants through the bed and can result in particle entrainment in the gas. Although these problems are less severe in beds fluidized with liquids rather than with gases, the fluidized particles still undergo a strong back-mixing process so that the bed behaves much like a continuous flow stirred-tank reactor. Although this turbulence may be desirable for certain processes such as heat exchange, it would be highly detrimental to any type of chromatographic separation.

As early as 1961, Hershler experimented with magnetic fields applied to liquid metals and magnetically susceptible solids which had been fluidized. He reported in the patent literature (U.S. Pat. Nos. 3,219,318 and 3,439,899) that a magnetic field created with an alternating current could be used to stir such liquid metals, fluidize beds even in the absence of a supporting gas or liquid stream, and (with several isolated fields in a column) decrease the bubbling and prevent material from being ejected from the top of a fluidized bed. The mechanisms of these actions apparently were not investigated to any great extent, and it is clear from the drawings in these patents that the magnetic fields were far from uniform.

Other work on magnetic fields in conjunction with fluidized beds was carried out by Tuthill (U.S. Pat. No. 3,440,731), however, it was not until the late 1970's when Rosensweig began publishing in this area that careful and systematic study of magnetically stabilized fluidized beds began ("Magnetic Stabilization of the State of Uniform Fluidization, *Ind. Eng. Chem. Fund.*, 18:260; "Fluidization: Hydrodynamic Stabilization With A Magnetic Field", *Science*, 204:57; and with Lucchesi, Hatch, and Mayer, "Magnetically Stabilized Fluidized Beds", *A.I.Ch.E. Symp. Series* 77, #205, 8). Among the important findings of Rosensweig and his co-workers are these: First, fluidization of magnetically susceptible solids can be stabilized in a uniform gradientless magnetic field in which the individual particles experience no net force. An axially-oriented field is preferred, although the orientation of the field is not crucial Second, stabilization is observed over a wide range of field strengths and fluidization velocities, and the applicable ranges of the important variables have now been mapped out by Rosensweig. For most fluid velocities, when the bed is stabilized, a decrease in magnetic field strength will result in normal fluidization while an increase will result in agglomeration of the solid particles. The effect of the magnetic field can be viewed roughly as creating a magnetic dipole in each particle which causes it to become "sticky" in a direction parallel to the field lines. This produces what amounts to chains of beads parallel to the axis of the bed.

As is the case in a ordinary fluidized bed, the particles in a magnetically stabilized fluidized bed behave as a fluid over a wide range of conditions. Their apparent density is greater than the fluid phase but less than the actual solid density. Unlike the ordinary fluidized bed, however, the dispersion and back-mixing of particulates is effectively zero. The magnetically stabilized fluidized bed is therefore an extremely interesting new phenomenon in its own right and is worthy of considerable further basic study. In addition, however, the properties of a magnetically stabilized fluidized bed are ideal for use in a continuous chromatography system. In this application, the fluid-like behavior of the solids would allow countercurrent solids/solvent contacting. Clogging by debris should be controllable, because the bed contents, along with debris that they filter out, can be continually removed and replaced All of these factors suggest chromatography in a magnetically stabilized fluidized bed would be a highly efficient separation scheme, and particularly in bioseparations because of the great need for improved processing of biomaterials; a fairly complex scheme such as this is most easily justified for products which have a high dollar value per pound. Prior to the present invention, however, the use of such technology has not been applied to these separations.

An examination of the support media presently available for use in a magnetically stabilized fluidized bed separation of biomaterials, however, was not successful. Prior to the present invention, there were no magnetic particles available which met the requirements for bioseparations, specifically these requirements of high density, accurate sphericity and uniform size, low porosity, and a high concentration of chemical groups which could be used to bind the affinity ligand through standard immobilization reactions. Metals such as nickel were lacking the last characteristic, and commercial composite materials were too low in density and too porous. The various requirements just listed were arrived at through a series of theoretical predictions and practical tests. In brief, they can be summarized by stating that the high density and moderately large size were necessitated by the use of a relatively dense and viscous fluidization phase, for example, water. The large size in turn dictated low porosity to prevent undesirable chromatographic band spreading from intra-particle diffusion delays Finally, a nonporous particle demands a high concentration of surface binding sites so that its adsorbing capacity is acceptably high.

Calcium alginate gels have been previously used as a biomaterial support for many different immobilized enzyme and cell preparation systems. The support is biochemically inert, easy to handle, and can be packed, like any other gel, into affinity chromatography columns. Immobilization (the techniques for which have been reported extensively) is usually accomplished by entrapment; the desired enzyme or cell population is mixed with the alginate solution and, upon polymerization, is "trapped" in the gel matrix. The gel itself offers little resistance to substrate diffusion.

For a number of reactions and separation systems, however, diffusion of into the interior of the support is either undesirable or impossible. Enzymes which react with large substrate molecules are wasted if they are immobilized in regions of the gel where the substrate cannot penetrate. Affinity cell separation systems which contain ligand dispersed in the support are likewise inefficient, since the cells only contact the surface of the gel. Systems such as these would be more efficient with the reactive species coupled only to the bead's surface.

Some separation techniques now being used also require magnetic supports to operate efficiently. High gradient magnetic filtration, for example, is one such technique which allows both filtering of lysed cell parts and purification of the enzyme being sought. In this technique the support with an affinity matrix attached is added to the disrupted cell mixture. The solution and support are then passed through a high gradient magnetic filter where the magnetic support is retained but the insoluble proteins and debris continue through. The field is then removed and the purified enzyme is obtained after desorption from the support. The supports used in the past for such separations have been metals or various gels with magnetic particles either adsorbed on their surface or dispersed throughout the gel matrix.

The support described in the present invention offers a new application of alginate in the biotechnology field. Although similar in some ways to others currently available, the beads have unique and highly desirable features. Alginate, the polymeric material from which the beads are made, is a block copolymer extracted from kelp consisting of $\beta$-D-mannuronate (M) and $\alpha$-L-guluronate (G) residues. Exposure to calcium ions in solution crosslinks the acid residues of the alginate molecules into a gel, producing a fairly stable support. When particles of magnetite ($Fe_3O_4$), a magnetic oxide of iron, are mixed with the alginate solution before gelation (a generalization of the process disclosed herein), the beads change from a cloudy white support to an opaque black magnetic support. When the beads are dried, the support shrinks irreversibly from the hydrogel state to a rigid solid while remaining quite spherical and highly magnetically susceptible. The density of the dried support is on the order of glass, but the reactivity is considerably greater. The porosity of the support is limited, but the exposed surface is microscopically very rough, providing many sites for protein or cell attachment.

It is, therefore, an object of the present invention to disclose a novel magnetic chromatographic separation support material.

It is further object of the present invention to disclose the use of a novel magnetic support material in affinity chromatography of bioproducts.

It is still a further of object of the present invention to disclose affinity chromatography of bioproducts carried out in a magnetically stabilized fluidized bed.

The following description of the drawing and examples are presented in order to allow for a more thorough understanding of the subject matter and experimental procedure of the present invention. The drawing and examples are meant to illustrate the embodiments of the present invention, and are not to be construed as limiting the scope of the invention.

DESCRIPTION OF THE PREFERRED EMBODIMENTS

Figure 1:
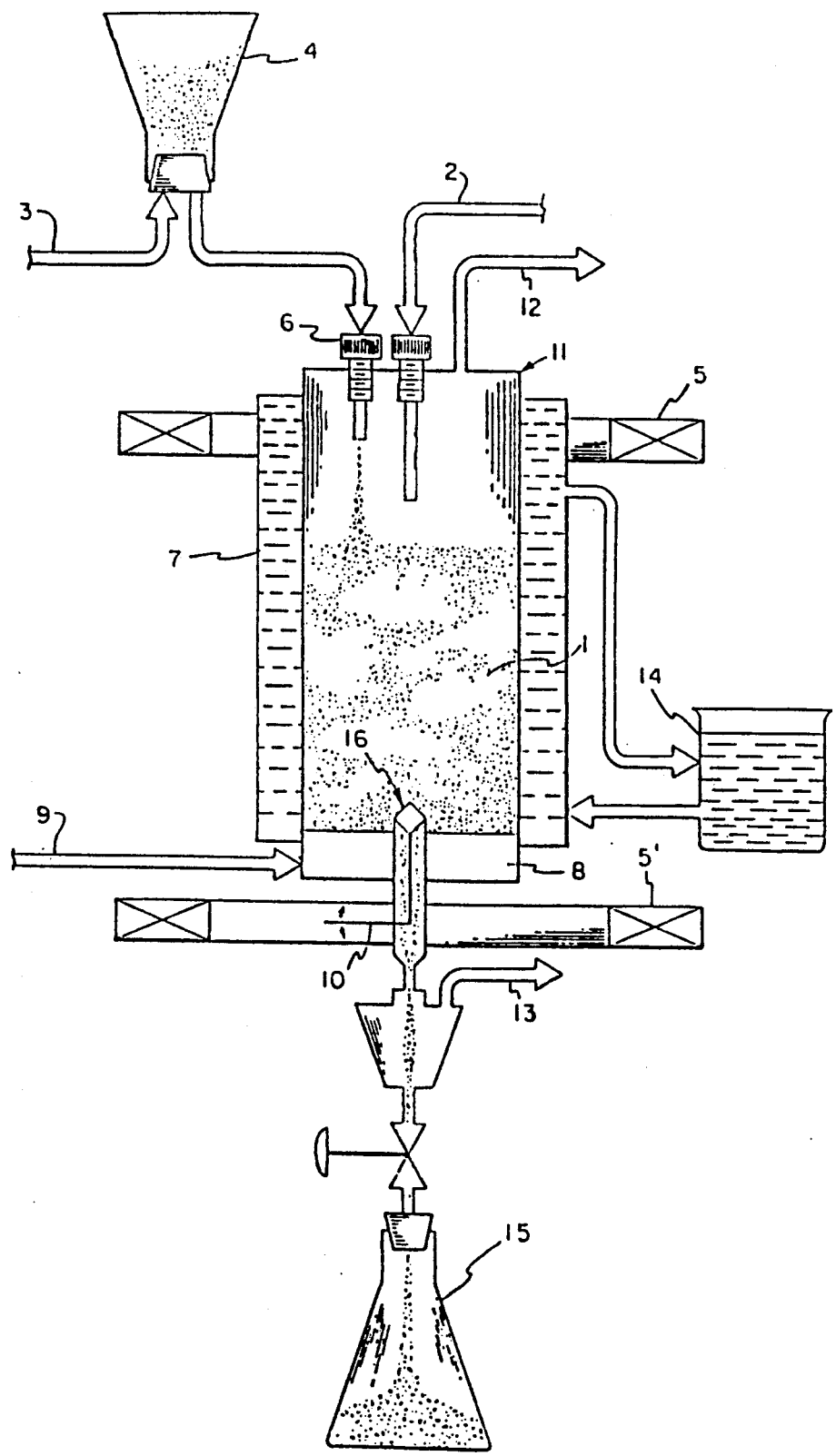
FIG. 1 is a schematic diagram of a magnetically stabilized fluidized bed chromatography system according to one embodiment of the present invention.

More particularly, FIG. 1 depicts the schematic representation of the magnetically stabilized fluidized bed chromatography system used to obtain the results in the experiments which follow. This system, however, may be modified to conform to other configurations, as for example, a system wherein the solids are recirculated, or wherein the solids and feed flow upwardly through the bed.

A number of these alternative forms may be found in the prior art as, for example, U.S. Pat. Nos. 4,283,204, 4,261,109, 4,272,893, 4,261,109, 4,247,987, 4,115,927, and the references cited therein. As depicted in FIG. 1, a magnetically stabilized fluidized bed 1 is contained in a chromatographic column 11. The column may be water-jacketed 7 by providing a constant temperature source 14 in order to maintain the temperature of the bed within set parameters. At the upper portion of the column is located an upper circular magnetic coil 5, and a lower circular magnetic coil 5' is located at the lower portion of the column. By controlling the current flowing through these coils, by adjusting the distances between the coils, and by varying the flow of solvent, solids, and feed, the integrity of the bed may be maintained.

In the examples which follow, a uniform magnetic field was created by this Helmholtz pair of coils which were found on forms having approximately a five inch inside diameter and approximately a seven inch outside diameter. The coils were approximately one inch thick, and were spaced two to three inches apart. The dimensions of the coils and number of turns in each were calculated to provide a uniform field. The column 11 was approximately one-half inch in diameter, and contains a bed 1 which is approximately four inches in length A stable D.C. power supply, variable over the range of 0 to 5 volts and capable of providing 1 ampere, was used to activate the coils at the low field strengths needed. Although these are the design parameters for the system shown in FIG. 1, obviously they may need to be modified according to the final application of the present invention, and such modifications are meant to be within the scope of the present invention.

In operation, solid chromatographic support materials, according to the present invention, and provided in a solids reservoir 4 or other supply means, are introduced into bed 1 by entraining the solids in a small amount of solvent stream 3. Both the solvent stream 3 and the feed stream 2 containing the crude bioproduct enter the column through individual adjustable ports 6 which may be raised or lowered to vary the relative lengths of the "enriching" and "stripping" sections of the column.

A solvent stream 9 enters at the lower portion of the column through a porous fluid distribution plate 8, passes through the bed, and exits through line 12.

At the lower portion of the column 11 is located a solids removal means 10 which, when activated, as for example by vertical movement as shown in the figure, raises or lowers a seal means 16 allowing the solids to be removed from the column. Of course, alternative means are also available for removing the solids from the column As the solids are removed, they are collected in a collection vessel 15, a further treated to elute the bound biomaterial, and are recirculated to the solids reservoir 4. An offline 13 is also included in the downflow stream between the seal 16 and the collection vessel 15 which allows the excess fluids coming off with the solids to be drained for either analysis or disposal.

As mentioned previously, prior to the development of the magnetically stabilized fluidized chromatographic system described above, there were not magnetic particles available which met the requirements for conducting bioseparations using this technology. The following examples describe a support media according to the present invention which meets the required criteria for the magnetically stabilized fluidized bed separation of biomaterials.

EXAMPLE I

Magnetite Preparation

A total of 12.8 g $FeCl_2$ .$4H_2O$ and 34.56 g $FeCl_3$ .$6H_2O$ was mixed in 1600 ml distilled water. This solution was then heated to 70 C and 32 g NAOH dissolved in 320 ml of distilled water was added. A black precipitate immediately formed and settled out after standing at room temperature for 1 hr. After part of the supernatant was aspirated, the remaining magnetite suspension was rinsed with several volumes of water (without drying) and transferred to a 500 ml volumetric flask. The amount of magnetite formed was calculated from the density of the magnetite/water mixture and the volume of the mixture was adjusted to form a 4.4% magnetite suspension. The magnetite could be resuspended at any time with vigorous shaking.

EXAMPLE II

Preparation of Beads

Fifty ml of 2% sodium alginate admixed with 50 ml of 4.4% magnetite solution was added to a 50 ml syringe equipped with a hypodermic needle. The syringe was slightly pressurized (less than 5 PSIG) with an external air supply and the solution added dropwise to 100 ml of 0.2 M CaCl solution approximately 50 mm below the tip of the needle. This procedure was repeated with another 50 ml of sodium alginate solution and the resulting mixture of 100 ml alginate beads and 100 ml $CaCl_2$ solution was stored for a period of at least 2 hours to permit complete reaction with $Ca^{++}$ions.

The resulting beads were placed in two 200 mm Petri dishes and rinsed several times with distilled water. The solution was then slowly aspirated using a Pasteur pipet and the support was air-dried in a hood 12 hrs. The beads were removed with gentle scraping, resulting in 3 ml of dried support.

(Nonmagnetic beads may also be prepared by substituting 50 ml of 1% sodium alginate solution for the alginate-magnetite solution. Without the magnetite, the total volume of the support following the drying procedure described previously was 1 ml).

The magnetic beads may also be prepared according to a number of different protocols. A number of these appear in Example III.

EXAMPLE III

Preparation Variations

Spraying — a 50/50 mixture of 4.4% magnetite and 2% alginic acid was prepared and placed in a 50 ml syringe. A 25 gauge needle was cut to a length of 2 mm and affixed to the end of the syringe. A high pressure (15-50 PSIG) was used to force the liquid out in a steady stream of 12 ml/min. This stream was directed at a solution of 0.2M $CaCl_2$ at an angle of 15° below horizontal and the resulting gel dried as previously described.

Stabilization — One ml of DuPont's Tyzor TE ®(-triethanolamine titanium chelate) solution was mixed with 1 ml 4.4% magnetite suspension and 2 ml 2% alginic acid. The liquid was quickly transferred to the syringe apparatus Tyzor TE ®rapidly hydrolyzes in an aqueous medium[7]) and dripped through a 21 G needle into 20 ml $CaCl_2$ containing an additional 2 ml Tyzor TE ®. After addition of 1-2 ml HCl (enough to reach pH 7) and reaction for 2 hrs., the beads were boiled for 1 hour (additional water being added as necessary) and dried in the normal fashion.

Blow drying — Approximately 10 ml of wet beads were blotted dry and placed in the syringe used to extrude drops. The air was connected to the needle end of the syringe while a porous cloth was affixed to the other end in place of the plunger. An air pressure of 10-15 PSIG was used to maintain a constant air stream up the center of the tube. Within 90 min the beads were dry.

The beads were examined under various conditions to characterize their behavior and structure.

Bead size and shape were analyzed by transferring 1-2 ml of dried beads to an 80 mm Petri dish and then placing the dish on top of a fluorescent light box. The macro-viewer assembly of a Cambridge Instruments Quantimet image analyzer was positioned above the dish and focussed to give a 15 ×15 mm field. The image obtained was edited and the projected area per bead calculated along with the roundness factor ([perimeter]$^2$/4[ou][projected area]). These calculations were repeated for at least four fields on each set of beads, analyzing between 15 and 133 beads total for each set. A mean square radius, a mean roundness factor and their standard deviations were calculated.

Bead density was measured by the following. A volumetric flask (10 or 25 ml) was filled to the calibration mark with distilled water and weighed. A number of beads was then added and the flask reweighed. Finally, water was aspirated until the original level was obtained and a third weight taken. The difference between the second and first readings was the weight of beads while the difference between the second and third readings, upon division by the density of water, was the volume.

Thermal characteristics were examined as follows. Wet and dried beads were placed on Petri dishes in a Fisher Isotemp over at settings from between 80° C. and 265° C. The beads were then examined for any size or color change and placed in a solution of carbonate buffer at pH 10 to check for dissolution or structural changes.

pH and salt affects were studied. Approximately 0.3 g of beads was placed in each of several 10 ml test tubes with 2.5 ml of various 0.1 M buffers and allowed to stand for 30 mins. to 25 hours. For medium to high pH solutions, two different buffers were used, one which contained calcium removal ions and one which did not.

Also, NaCl, at several concentrations was used in separate tubes. For each case, the size and rigidity of the support was examined.

Mechanical affects were studied. Each bead tested was placed on an Ainsworth electronic balance and the flat end of a 2 cm diameter glass rod was used to compress the beads under manual pressure. A force was read when the height of the bead was reduced to approximately half its original value. The balance utilizes a magnetic field servo system for weighing so that very little if any pan deflection occurred curing this procedure.

Magnetic affects were studied. 1.13 g of dried 0.9 mm diameter magnetic beads were placed in a vial 0.6 cm ×3 cm and inserted into an 60 Hz oscillating magnetic field. M vs H measurements were made at 77 K (liquid nitrogen temperature) and 300 K.

Surface Structure was examined. Magnetic beads made with a 21 G needle and air dried on a Petri dish were glued to a 1 mm diameter support and vacuum shadowed with gold for scanning electron microscopy. Once the apparatus was initialized and calibrated, pictures were taken at magnifications of 40×, 1250× and 10,000×. At 1250× magnification, two photographs were taken, one at 14° and one at 20° from vertical to obtain a stereoscopic air.

Pore Structure was determined. Steady state porosity measurements were made using a solution (approx. 0.3 g/ml, absorbance of 0.79) of crystallized egg albumin as the penetrant. Known volumes of beads and albumin solution were mixed and allowed to equilibrate overnight. An absorbance reading of the supernatant solution was taken using an ISCO UA-4 absorbance monitor. The bead volume accessible to molecules of size similar to that of albumin (0.01 m dia.) was then calculated.

Results of Table I presents the density and mechanical strength studies. Clearly, the strength of the dried magnetic beads was far superior to either of the wet gels. The strength did depend on the condition of the beads, whether they had been stored dry or whether they had been immersed in water for a period of 24 hours (labelled "rehydrated" in the table), indicating some strength loss due to the slight swelling observed.

TABLE I

| BEAD | DENSITY (g/ml) | CRUSH FORCE TO ½ DIA. (G) |
|---|---|---|
| Non-magnetic, wet | 1.06 | 7 |
| Magnetic, wet | 1.10 | 20 |
| Non-magnetic, dried | 1.7 | — |
| Magnetic, dried | 2.2 | 1000 |
| Magnetic, dried (rehydrated) | — | — |

TABLE I - Density and mechanical strength of calcium alginate beads which were extruded in drop form from a 21G needle.

The mechanical properties of the non-magnetic wet gel are similar to those of dextran or polyacrylamide of comparable percent solids, while the strength of the wet magnetic gel was slightly greater. The wet Tyzor-stabilized gel was less elastic then the other two alginate gels, disintegrating when compressed instead of merely flattening.

The magnetic properties of the beads proved to be attractive. Plots of M (magnetization) vs. H (magnetic field strength) revealed that while having a relatively high magnetization, the beads retain some super-paramagnetic properties characteristic of small magnetic particles. Super-paramagnetic implies that the magnetic moments of the magnetite particles are small enough to fluctuate rapidly by thermal vibrations. The beads will have little if any remanent magnetization when the field is removed, a decided advantage in most applications. This hypothesis is confirmed by noting the small hysteresis loop of M vs. H at room temperature compared to the loop at liquid nitrogen temperature. I has been previously reported residual magnetism in polyacrylamide/magnetite beads caused undesirable bead agglomeration. Although a small number of beads according to the present invention remained slightly magnetized after removal from the field less than 3 emu/g), the particles did not agglomerate.

The surface structure of the support as revealed at 40× magnification appears quite spherical with only minor flat spots due to drying on the Petri dishes. At 1250× magnification detailed surface structure and surface irregularities are seen. At 10,000× magnification, the valleys in the surface seem to be about 2–5 microns wide and at least 2 microns deep. The surface is thus quite rough, providing a large exposed surface area for attachment of many enzymes, biomolecules, and cells.

The porous nature of the beads was investigated using steady state albumin permeation. The penetration of this protein into the beads revealed the porosity values listed in Table II. While normal calcium alginate beads were found to be relatively porous, undried magnetite beads were slightly less porous, undoubtedly due to the internal volume of the bead occupied by magnetite particles. The dried spheres, by albumin porosity measurements, were essentially impermeable. However, a porosity of 5% or less would have been obscured by measurement error. Also, since the beads are soft and do expand very slightly after rehydrating, it is possible that some pores of smaller size are present.

TABLE II

| BEAD | Porosity (%) |
|---|---|
| Non-magnetic, wet | 55 |
| Magnetic, wet | 25 |
| Magnetic, dried | less than 5 |

TABLE II - Porosity of various calcium alginate beads extruded in drop form from a 21G needle as calculated from albumin penetration.

Although the shape of the dried magnetic beads was quite spherical and the size was reproducible, there are a number of factors which influence these parameters. One factor is the method used to extrude the alginate solution from the hypodermic needle. When extruded in drop form, the size of the beads produced could be predicted from the size of the needle (Table III),

TABLE III

| Hypodermic Gauge | Mean Area (mm$^2$) | Mean Roundness | Mean Sq. Diam. (mm) |
|---|---|---|---|
| 18 | 0.749 ± 0.038 | 1.05 ± 0.03 | 0.98 ± 0.02 |
| 20 | 0.549 ± 0.044 | 1.06 ± 0.03 | 0.84 ± 0.03 |
| 21 | 0.608 ± 0.033 | 1.04 ± 0.01 | 0.88 ± 0.02 |
| 22 | 0.536 ± 0.044 | 1.06 ± 0.03 | 0.83 ± 0.03 |
| 23 | 0.455 ± 0.044 | 1.05 ± 0.03 | 0.76 ± 0.04 |
| 25 | 0.358 ± 0.027 | 1.06 ± 0.03 | 0.68 ± 0.02 |

TABLE III - Size and shape of dried calcium alginate/magnetite beads extruded in drop form from various gauge hypodermic needles.

and the flow rate of solution (Table IV).

TABLE IV

| Drops/sec | Mean Area (mm²) | Mean Roundness | Mean Sq. Diam. (mm) |
|---|---|---|---|
| 1 | 0.497 ± 0.033 | 1.04 ± 0.02 | 0.80 ± 0.02 |
| 2 | 0.567 ± 0.039 | 1.04 ± 0.02 | 0.85 ± 0.03 |
| 3 | 0.624 ± 0.040 | 1.04 ± 0.02 | 0.89 ± 0.03 |
| 4 | 0.656 ± 0.046 | 1.05 ± 0.03 | 0.91 ± 0.03 |
| 5 | 0.643 ± 0.051 | 1.04 ± 0.03 | 0.90 ± 0.04 |
| 6 | 0.710 ± 0.043 | 1.04 ± 0.02 | 0.95 ± 0.03 |
| 8 | 0.693 ± 0.052 | 1.05 ± 0.03 | 0.94 ± 0.03 |
| 10 | 0.720 ± 0.054 | 1.04 ± 0.02 | 0.96 ± 0.03 |

TABLE IV - Size and shape of dried calcium alginate/magnetite beads extruded in drop form from a 21G hypodermic needle at different flow rates.

When this flow rate was increased out of this particular regime so that a spray of small droplets was formed, beads of considerably smaller sizes were made (TABLE V).

TABLE V

| Flow Rate (ml/min) | Mean Area (mm²) | Mean Roundness | Mean Sq. Diam. (mm) |
|---|---|---|---|
| 1.8 (7 drops/sec) | 0.358 ± 0.027 | 1.06 ± 0.03 | 0.68 ± 0.02 |
| 12 (spray) | 0.055 ± 0.024 | 1.10 ± 0.03 | 0.26 ± 0.05 |

TABLE V - Size and shape of dried calcium alginate/magnetite beads extruded in spray and drop form from a 25G hypodermic needle.

The disadvantage of this technique is that the homogeneous size of the support achieved by dropwise production is lost. The diameter of the beads formed in a dropwise manner has a standard deviation of only about 3%, but that of the spray-formed beads is almost 20%.

The correct calcium concentration is essential for optimum crosslinking of the polymer chains. Calcium, however, is another factor that governs the shape of both the wet and dried beads. A low calcium as they pass through the surface of the polymerizing solution, but these tails are eliminated when the $Ca^{++}$ concentration is raised. Other ions used in the receiving solution, such as $Fe^{3+}$, $Mg^{2+}$ and $Mn^{2+}$ formed spherical beads but their rigidity was not as good as that of the calcium alginate spheres. Even a highly acidic solution made with HCl was able to form a gel.

The method of drying probably has the most noticeable effect on the shape of the beads. If the magnetic spheres were left in a beaker to dry, the resulting small beads agglomerated, making separation difficult. However, if just enough wet beads to form a monolayer were placed in a Petri dish, the dried beads obtained were isolated spheres which were easily removed. The major draw of this drying technique was that small "flat spots" formed where the beads touched the glass surface. The size of this flat spot on magnetic beads varied. When non-magnetic alginate beads were used, however, the flat spot was so pronounced that flat discs instead of round spheres formed.

Drying in Petri dishes at elevated temperatures of 80° C. and 120° C. did not eliminate this flat spot, but did not decrease the time necessary for drying (60 min. and 15 min. respectively, as opposed to approximately 10 hours for aid drying). But if the beads were dried or heated above 160° C. and then dissolved as described previously, the supernatant solution was yellow-orange, indicating that the calcium alginate had been affected by the extreme heat.

In some applications such as High Pressure Liquid Chromatography (HPLC), an accurate spherical shape and monodisperse size are necessary for optimum resolution. We, therefore, developed a technique to eliminate irregularities caused by drying. Using a continuous air stream as described in Example III, we produced magnetic beads which did not contain a flat spot and where seemingly perfect spheres. If nonmagnetic beads were dried in a similar fashion, irregular roughly spherical beads were obtained.

The stability of the dried beads in aqueous solutions and other solvents was an important consideration. If, upon addition to a solvent, the beads merely swelled to their original size, then the unique properties described here would be irrelevant. To examine these properties, a sample of beads was placed in distilled water and the solution stirred for a week. At least daily the water was removed and replaced with fresh distilled water to test for disruption by calcium diffusion. At the end of this period, the beads were still rigid and could not be crushed between one's fingers. The beads swelled about 1% when first placed in water, but no further changes were seen thereafter. Soaking the beads in solvents such as methanol and acetone brought about similar results.

Other substances, though, can damage the bead's structure. Table VI shows effects of various buffer solutions at several different pH values.

TABLE VI

| pH | Buffer System | Bead Reaction |
|---|---|---|
| 0-2 | HCl | Magnetite dissolved |
| 4 | Phthalate | Swell 1% |
| 7 | Phosphate | Bead dissolved |
| 7 | Tris* | Swell 100% plus |
| 7 | Tris* + $CaCl_2$ | Swell 1% |
| 8 | Tris* | Swell 100% plus |
| 8 | Tris* + $CaCl_2$ | Swell 1% |
| 9 | Boric acid | Swell 1% |
| 10 | Carbonate | Bead dissolved |
| 10 | Boric acid | Swell 1% |
| 11 | Boric acid | Swell 1% |
| 12-14 | NaOH | Swell 1% |

*Tris = Tris (Hydroxymethyl) Aminomethane
TABLE VI - Stability of dried calcium alginate/magnetite beads in aqueous solutions. Beads were extruded in drop form from a 21G hypodermic needle.

Although some buffers caused dissolution of the beads, at least one buffer solution was found at each pH which would not dissolve the beads or affect their structure. For all cases tested, if addition of $CaCl_2$ to a buffer solution produced a calcium precipitate, then the buffer solution also removed the calcium from the beads and thus dissolved them. Calcium chelating agents such as EDTA also dissolved the beads. Other solutions, such as multivalent metal ions or NaCl at high concentrations weakened the structure of not only the wet alginate gels but the dried spheres as well. For solutions which merely swelled or softened the beads, the addition of small amounts of $CaCl_2$ usually eliminated this problem.

The nonmagnetic dried beads' properties were not as attractive as those of the magnetic spheres. In almost all solutions, the beads increased at least 20% in size and became quite soft. However, in some solutions (such as pH 7: tris buffer solution with $CaCl_2$ added) the beads did not lose their rigid shape or expand more than about 5%. It appears the addition of magnetite to the alginate solution strengthens the bead's overall structure.

Although these magnetic beads are stable in many different solutions, a technique to introduce additional crosslinking using another material seemed imperative for certain applications (phosphate and other typical buffer ions destroy the support). Glutaraldahyde and other agents were unsuccessful as crosslinkers, but a DuPont product called Tyzor TE ® was effective. The Tyzor-treated beads made as described previously resisted carbonate buffer at pH 10 and other calcium chelating agents, providing a sturdy support capable of withstanding a large variety of conditions. Of course, not all materials were tested as crosslinkers, and it is not the intent of the present invention to be limited solely to Tyzor$^{TE}$. Epichlorohydrin, for example, has been reported as a technique for stabilizing nonmagnetic wet calcium alginate beads, and this material may also have utility in stabilizing the magnetic beads as well.

A number of experiments were carried out to demonstrate the usefullness of the magnetic beads according to the present invention as a biomaterial support.

Protease from *Actinomyces fradiae* was immobilized on dried calcium alginate/magnetite beads using known techniques with both glutaraldehyde and TiCl$_3$ and assayed for activity.

TABLE VII

| Coupling method | Metal ion | Activity unit/g of support |
| --- | --- | --- |
| Glutaraldehyde | — | 50.0 |
| Glutaraldehyde | $Cu_{++}$ | 61.0 |
| Glutaraldehyde | $Zn_{++}$ | 43.0 |
| Glutaraldehyde | $Co_{++}$ | 35.0 |
| Glutaraldehyde | $Cd_{++}$ | 25.0 |
| Glutaraldehyde | $Mn^{++}$ | 0.0 |
| TiCl$_3$ | — | 5.0 |

TABLE VII - Activities of *Actinomyces fradiae* protease immobilized on magnetic support. The beads used were extruded in drop form from a 21G needle and dried. Concentration of all metal ions used was 0.013 M.

These activities compare favorably with activities obtained on other supports ranging from 2.4 to 102 units/g carrier with an average of 44 units/g carrier. For each method used, it was possible to couple 20–25 mg of protease per gram of support.

α-amylase was also coupled to the support according to the present invention with the same immobilizing compounds.

TABLE VIII

| Coupling method | Metal ion | Activity unit/g of support |
| --- | --- | --- |
| Glutaraldehyde | — | 68 |
| Glutaraldehyde | $Ca^{++}$ | 133 |
| TiCl$_3$ | — | 78 |
| TiCl$_3$ | $Ca^{++}$ | 167 |

TABLE VIII - Activities of *Aspergillus niger* α-amylase immobilized on magnetic support. The beads used were extruded in drop form from a 21G needle and dried. Concentration of calcium ions used was 0.013 M.

This immobilization in the presence and absence of calcium was interesting to investigate because α-amylase from *Aspergillus niger* is a calcium-containing enzyme. If the enzyme loses calcium, then it looses activity as well. Immobilization in the absence of calcium is usually unsuccessful, but the presence of calcium in the support according to the present invention produced bound protein with a relatively good activity. Addition of extra $Ca^{++}$ ions during immobilization increased this activity, but not the total amount of bound protein (residual activity was about 45%). Activities of other α-amylases bound to a number of supports ranged from 15 to 4500 U/g with an average of around 200 U/g. An average of 20 mg of α-amylase was coupled for each gram of support.

The temperature optimum of immobilized x-amylase was the same as that for the soluble enzyme (55° C.) and the pH optimum and pH stability of both x-amylase and protease were not changed. Ten-fold repetition of the specific reaction on 5% substrates did not change the activities of α-amylase and proteases immobilized to the support. It was concluded from these results that the immobilization of these enzymes to calcium alginate/magnetite beads did not affect the enzymes properties appreciably.

In view of the results obtained in the immobilization of enzymes, the potential usefullness of the magnetic beads according to the present invention became apparent.

Before using the magnetic beads in an affinity chromatographic separation, however, it is necessary to attach a "binding ligand" to the bead which will act to bind the bioproduct to the bead. Although a number of these materials are known (see for example the listing of such materials by Dean and Watson, "Protein purification using immobilized triazine dyes", J. of Chromatography, 165:301, the disclosure of which is incorporated herein by reference), the specific dye Cibacbron Blue F3G was chosen because it is well known that only a certain very restrictive range of proteins (those with the "dinucleotide cleft") will be bound by this dye. It would be possible, therefore, to separate the test protein, human serum albumin (HSA) from a mixture of other materials. Of course, other binding materials such as, for example, antibodies (such as monoclonal antibodies) may be substituted for the dye.

The addition of the dye to the magnetic bead of the present invention was accomplished as described in the following example.

EXAMPLE IV

Cibacron Blue F3GA Dye attachment was achieved by a modified form of Bohme's procedure. Magnetic dried beads (1.4 g) were placed in 48 ml H$_2$O and heated to 60° C. Cibacron Blue F3GA (0.27 g) in 8.2 ml distilled water was added dropwise and the solution stirred for 30 min. Calcium chloride (7.9 g) was added and the mixture stirred for an additional hour. At this point, the temperature was increased to 80° C. and 0.2 g NaOH in 2 ml H$_2$O added. After two (2) hours of stirring, the support was extensively washed with a 6M urea and 1M CaDl$_2$ solution until no blue color was observed leaching from the beads.

EXAMPLE V

Separation Using Alginic Acid-Magnetite Beads with Attached Cibacbron Blue F3G to remove Albumin from solution.

A plexiglas column ½" in inside diameter and 4" long was used for the separation. The column was situated in the center of a pair of coils, each of which had an inside diameter of 5½" an outside diameter of 7½" and a width of ¾". The coils were placed 2½" apart. Each coil had approximately 300 turns, and a current of 1.3 amps produced a field strength of about 40 Oersteds.

Calcium Alginate-Magnetite-Cibacbron Blue beads of a diameter about 200 microns were added to the column automatically to maintain a bed height of 50. cm. They were removed at the bottom by an automatically pulsed solids valve at a rate of 0.3 to 0.6 g/min. Solvent (Tris/HCl 0.05M pH8 plus 0.05M CaCl$_2$ in H$_2$O) was injected into the base of the column at 10 to 15 ml/min. The feed was human serum albumin (HSA) at a concentration of 1 mg/ml in the same solution as the solvent. It entered the column at the same location as the feed at rates from 0.2 to 1.0 mg albumin/min.

Liquid was removed from the top of the column at a rate of 8 to 13 ml/min.

For case 1 (1 mg albumin/min., solids flow 0.3 g/min), analysis of the exiting liquid and solids streams showed that about 40% of the albumin was adsorbed in a contact time of 30 seconds. When the albumin was brought in at a lower rate of 0.2 mg./-min., and solids passed through the column at 0.6 g/min. all of the albumin was adsorbed by the solid beads.

In summary, the present invention has shown that dired spheres made from an alginate solution containing magnetite particles have excellent potential as a support for enzyme immobilization and chromatographic applications. The beads were found to be much stronger than gels such as polyacrylamide and dextran, indicating that high flow rates and pressures could be used in column separations. The support withstood not only temperatures of up to 120° C., but also most pH values and common solvents. While some solutions, such as phosphate buffers, dissolved the spheres, stabilization eliminated this problem. The physical properties of the beads include a glasslike density of 2.2 g/ml, excellent sphericity, low porosity, and a narrow size distribution. The magnetite present in the support allows the beads to be used for magnetic separations such as high gradient magnetic filtration. Their high degree of micro-roughness provides a large exposed surface area for enzyme and ligand binding. Mixed *Actinomyces fradiae* proteases and *Aspergillus niger* α-amylase, two enzymes representative of classes which attack large substrates, were immobilized on the bead's surface with high activity and stability. A cyanuric dye which can be used in chromatographic applications was also readily coupled to the surface of this support with good yield. In short, the magnetic bead supports of the present invention should have a wide range of applications in bioseparation and immobilized biochemical technology.

Thus, while we have illustrated and described the preferred embodiment of our invention, it is to be understood that this invention is capable of variation and modification, and we therefore do not wish to be limited to the precise terms set forth, but desire to avail ourselves of such changes and alterations which may be made for adapting the invention to various usages and conditions. Accordingly, such changes and alterations are properly intended to be within the full range of equivalents, and therefore within the purview, of the following claims.

Having thus described our invention and the manner and process of making and using it, in such full, clear, concise, and exact terms so as to enable any person skilled in the art to which it pertains, or with which it is most nearly connected, to make and use the same;

We claim:

1. A method for the manufacture of a mechanically rigid and generally spherical bead having an interior generally comprising a magnetically susceptible material having low residual magnetiziation, and an exterior generally comprising a material capable of binding with bioproduct materials, wherein said bead has low residual magnetization, a rough surface structure, a diameter at least about 200 $\mu$m., and a porosity of less than about 5% when in a dried state, comprising the steps of:

admixing an alginate solution with a plurality of particles which comprise a magnetically susceptible material having low residual magnetization; and
   cross-linking the alginate acid residues of said alginate solution into a gel to form said bead; and
   drying said bead.

2. The method of claim 1 wherein the alginate solution is prepared from sodium alginate.

3. The method of claim 1 wherein the particles comprise magnetite.

4. The method of claim 1 wherein the cross-linking agent comprises calcium ions.

5. The method of claim 1 further comprising attaching a binding ligand to the cross-linked support material.

6. The method of claim 5 wherein the ligand is a triazine dye.

7. The method of claim 5 wherein the ligand is a an antibody.

* * * * *